(12) United States Patent
St. Germain

(10) Patent No.: US 7,222,546 B2
(45) Date of Patent: May 29, 2007

(54) METHOD AND APPARATUS FOR SEDIMENT CHARACTERIZATION

(75) Inventor: Randy St. Germain, Fargo, ND (US)

(73) Assignee: Dakota Techologies, Inc., Fargo, ND (US)

( * ) Notice: Subject to any disclaimer, the term of this patent is extended or adjusted under 35 U.S.C. 154(b) by 0 days.

(21) Appl. No.: 11/257,772

(22) Filed: Oct. 25, 2005

(65) Prior Publication Data
US 2006/0086173 A1  Apr. 27, 2006

Related U.S. Application Data

(60) Provisional application No. 60/622,075, filed on Oct. 26, 2004.

(51) Int. Cl.
*G01N 1/00* (2006.01)

(52) U.S. Cl. .................. 73/863.21; 73/863.23

(58) Field of Classification Search .......... 73/863.21, 73/863.23, 864.31, 863.24, 863.31, 874.71, 73/864.64
See application file for complete search history.

(56) References Cited

U.S. PATENT DOCUMENTS

| | | | | |
|---|---|---|---|---|
| 3,715,913 A | * | 2/1973 | Anderson | 73/61.71 |
| 4,745,801 A | * | 5/1988 | Luzier | 73/152.23 |
| 5,604,582 A | * | 2/1997 | Rhoads et al. | 356/73 |
| 5,611,671 A | * | 3/1997 | Tripp, Jr. | 417/126 |
| 6,097,785 A | * | 8/2000 | Elam | 378/45 |
| 6,401,547 B1 | * | 6/2002 | Hatfield et al. | 73/861.04 |
| 6,742,406 B2 | * | 6/2004 | Dostie | 73/864.64 |
| 6,823,749 B1 | * | 11/2004 | Welsh et al. | 73/864.64 |
| 6,865,933 B1 | * | 3/2005 | Einarson et al. | 73/152.23 |
| 2002/0035303 A1 | * | 3/2002 | Chu et al. | 570/238 |

OTHER PUBLICATIONS

"The GORE-SORBER Module", Oct. 2004, www.SoilGasSurveys.com, (corresponds to device in paragraph [007] in the background section of the application as filed.

* cited by examiner

*Primary Examiner*—Robert Raevis
(74) *Attorney, Agent, or Firm*—Dorsey & Whitney LLP

(57) ABSTRACT

A method for characterizing contaminants within sediment comprising positioning a sampler in a continuous manner within the sediment, exposing the sampler to the sediment for a dwell time, retrieving the sampler, and analyzing the sampler. The sampler is exposed to the sediment for a sufficient period of time to allow at least one analyte of interest to permeate the sampler. The sampler may be analyzed using fluorescence and/or gas chromatography/mass spectrometry to determine contamination versus sampler length. The contamination versus sampler length may be converted to contamination versus depth or contamination versus horizontal position.

13 Claims, 10 Drawing Sheets

METHOD AND APPARATUS FOR SEDIMENT CHARACTERIZATION

FIELD OF THE INVENTION

This invention relates generally to sediment characterization, and more specifically to methods and apparatus for depth-continuous characterization of contaminants within sediment.

BACKGROUND OF THE INVENTION

It is often desirable to characterize distribution of contaminants, such as polycyclic (or polynuclear) aromatic hydrocarbons (PAHs) or polychlorinated biphenyls (PCBs), in sediment.

Traditional sampling and analyses approaches, such as direct-push or drilling and sampling technologies, which may be relatively cheap and routine and may meet quality assurance/quality control (QA/QC) standards are more expensive and difficult when conducted on or in water environments. What is routine on dry land becomes difficult and often suffers from questionable QA/QC due to compacting of the sediments, poor recovery as a result of running sands, pudding-like slurries, etc. For example, in sand or slurry, it may be difficult to obtain a continuous core for sampling. When obtaining samples and analyzing samples, portions of the sediment are removed. These portions must be handled, cataloged and stored. Generally, several points in a site are sampled and analyzed. A map of contaminant concentration is generated based upon these points. Due to the expense of gathering sampling data, maps are frequently generated on the basis of relatively few data points.

Solid-phase extraction (SPE) techniques have been developed to, for example, analyze sediment that has been sampled or to avoid requiring sediment sampling.

One currently available SPE approach is the GERSTEL-Twister offered by GERSTEL GmbH & Co. The GERSTEL-Twister is a stir bar coated with polydimethyl siloxane (PDMS). The GERSTEL-Twister is used to stir a sediment sample. Semi-volatile organics in liquids or slurries are sorbed into the PDMS during stirring. The stir bar is rinsed and thermally desorbed, cryogenically focused and transferred to a GC column for analysis.

Another SPE approach uses an Empore disk, commercially available from 3M. Empore disks are self-contained SPE devices that adsorb PCBs from solution. The disks comprise a C-18 sorbent material held in an inert matrix (PTFE). The disks are used in a laboratory setting to isolate/capture PCBs and PAHs in sediments and fluids.

One SPE approach for passive-sampling, or analyzing sediment without requiring removing samples of sediment, is the Gore-Sorber from W.L. Gore & Associates, Inc. The Gore-Sorber comprises a continuous water impermeable membrane surrounding a sorbent material. The Gore-Sorber is delivered into the vadose zone. Volatile organic compounds (VOCs) from groundwater, soil gas, or air permeate through an outer hydrophobic membrane and are trapped on adsorbent material located inside. After a predetermined time, the Gore-Sorber is removed from its sampling location and sent to a laboratory where the VOCs are removed from selected sections (snips) of the Gore-Sorber and analyzed.

Another SPE approach for passive-sampling is the Flexible Liner Underground Technologies, Ltd. Co. (FLUTe). A specialized version of FLUTe, called the NAPL FLUTe system, is used to locate layers, filled fractures or globules of chlorinated solvent product trapped in formation. The FLUTe is placed in a punched or drilled hole where a dye in the liner reacts with the dense non-aqueous phase liquid (DNAPL) to produce a stain. When the liner is removed, the stains on the FLUTe surface indicate the location of NAPL in the hole. The FLUTe thus provides a visual indicator of presence of NAPL but does not provide more than presence/no presence capability.

Determining spatial distribution of and performing analyses on contaminants in sediments is difficult. Large-scale dredging plans may be drafted based on relatively few continuous coring and Gas Chromatography/Mass Spectrometry (GC-MS) analyses locations. This is because forming a coherent picture of contaminant distribution at a single sampling location is frequently complicated using currently available methods.

A less laborious and less expensive characterization process would enable leaving resources for remediation and treatment of the contaminated area.

SUMMARY OF THE INVENTION

A method for characterizing contaminants within sediment comprises positioning a sampler in a continuous path within the sediment, exposing the sampler to the sediment for a dwell time, retrieving the sampler, and analyzing the sampler. The sampler comprises a linear segment of absorbent material and is exposed to the sediment for a sufficient period of time to allow at least one analyte of interest present along the path to permeate the sampler. The sampler is removed from the sediment and analyzed for contaminant concentration. Analysis may be of one or more points along the sampler or may be done continuously along a sampler segment.

While multiple embodiments are disclosed, still other embodiments of the present teachings will become apparent to those skilled in the art from the following detailed description, which shows and describes illustrative embodiments. As will be realized, the teachings are capable of modifications in various obvious aspects, all without departing from the spirit and scope of the present teachings. Accordingly, the drawings and detailed description are to be regarded as illustrative in nature and not restrictive.

DETAILED DESCRIPTION OF THE INVENTION

The sampling methods and apparatus disclosed may be used for characterization of contaminants in sediment. The contaminants may be, for example, polycyclic aromatic hydrocarbons (PAHs), polychlorinated biphenyls (PCBs), semivolatile organic compounds (SVOs), volatile organic compounds (VOCs), metals, inorganic ions, biological materials (e.g., proteins, viruses, bacteria, etc.), gases, or other analytes of interest.

Figure 1:
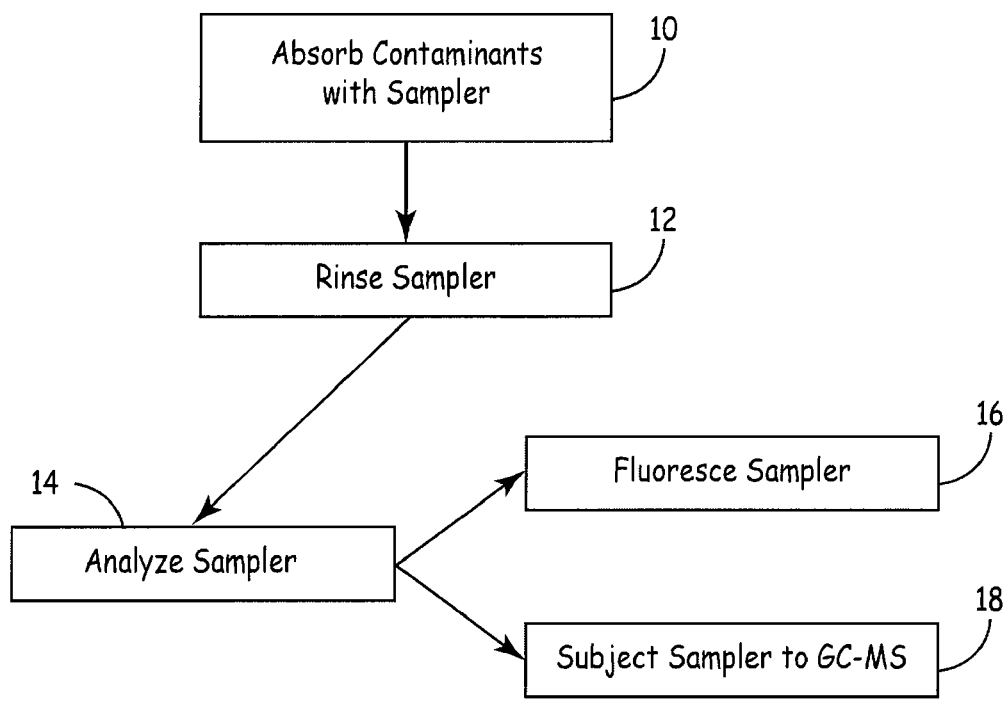
FIG. 1 is a block diagram of a method of sediment characterization in accordance with one embodiment of the present invention.

FIG. 1 illustrates a block diagram of a method of sediment characterization. As shown, the method of sediment characterization comprises sampling contaminants from the sediment using an absorbent sampler and analyzing the sampler after absorption of contaminants to determine contamination (for example by PAHs or PCBs) versus linear position. This analysis may then be converted to contamination versus sediment layer, depth or horizontal position.

Generally, contaminants are absorbed using the sampler, shown at block 10. Thus, as will be described more fully below, the sampler is placed to absorb contaminants along an area of interest and, after adsorption, the sampler is removed. The sampler is rinsed, shown at block 12, and analyzed, shown at block 14. Analysis may comprise fluorescing the sampler, shown at block 16, or subjecting the sampler to GC-MS, shown at block 18.

Figure 2:
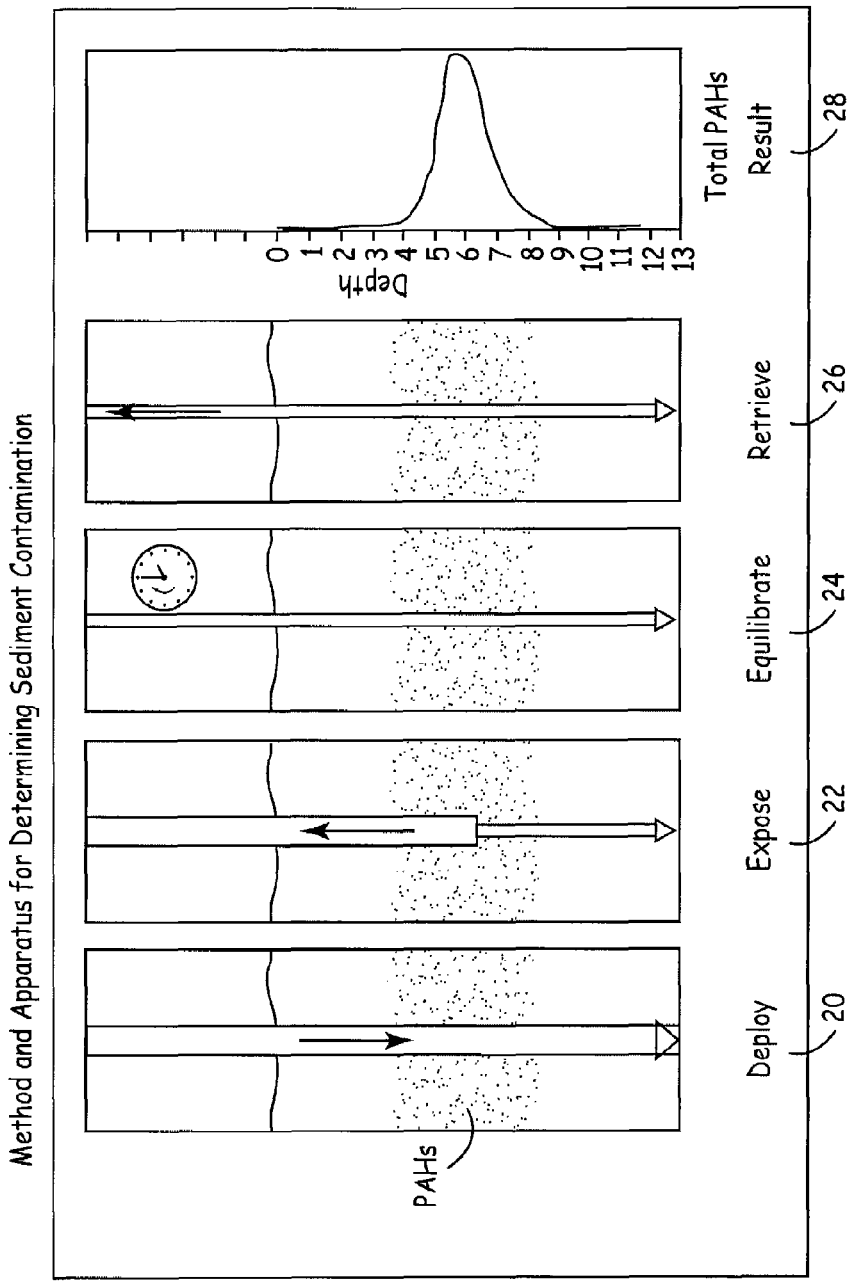
FIG. 2 is a diagram of using a sampler in accordance with one embodiment of the present invention.

The general methods of using a sampler are shown in FIG. 2. As shown, the sampler is deployed along a prescribed path, exposed, allowed to equilibrate, and retrieved. Thus, initially an area of interest, for example a river, bay, or estuary suspected of contamination, is located and one or more sampler(s) deployed at a position in that area. Deployment, shown at block 20, involves positioning the sampler to a depth in the sediment. The sampler(s) may be deployed with a sheath or protective layer extending thereabout to prevent absorption of contaminants into the sampler during deployment. Exposing the sampler, shown at block 22, involves removing the sheath or protective layer, if used, to expose the absorbent sampler to the sediment. Equilibrating, shown at block 24, involves allowing the sampler to be exposed for a dwell time. After the dwell time, the sampler is retrieved by removing the sampler from the sediment, shown at block 26, and analyzed. A log may then be generated of contaminant level versus depth or horizontal position, shown at block 28.

Description of Sampler

Figure 3:
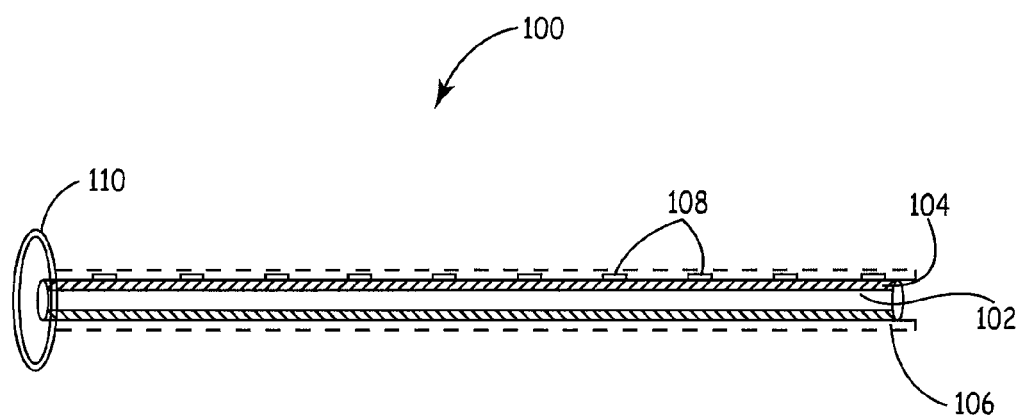
FIG. 3 is a diagram of a segment of a sampler in accordance with one embodiment of the present invention.

FIG. 3 diagrammatically illustrates an absorbent sampler 100. The absorbent sampler 100 comprises a support 102 coated with an absorbent material 104 (or solid phase extraction media). Alternate embodiments will be obvious to one skilled in the art and are within the scope of the present invention. For example, a support such as a solid rod may be used wherein the rod is inserted into tubing of absorbent material. Such support may be temporary and act as a delivery rod. Optionally, a protective layer or sheath 106 may be provided over the absorbent material 104. The absorbent material 104 may be a semipermeable material or a membrane which is permeable to the analyte(s) of interest but which excludes some other compound or analyte. Driven by a pressure, concentration, temperature, or other chemical potential, the analytes may cross into the absorbent material by various mechanisms.

Thus, the absorbent sampler 100 may comprise a support 102 coated or permeated with an absorbent material 104 such as silicone (polydimethyl-siloxane or PDMS). Contaminants such as PAHs are absorbed into silicone as though the silicone were a solid solvent. Considerations in choosing other suitable materials for use as the absorbent material 104 include the optical clarity of the material, the background fluorescence of the material, the durability of the material, the binding of the material to the support, and the deliverability of the material. For example, if fluorescence is to be used for analysis, it may be desirable to have an absorbent material with near zero autofluorescnece combined with a very high fluorescence when exposed to an analyte of interest (for example PAH non-aqueous phase liquids such as coal tar or oil). Other materials may include, by way of example and not limitation, cellulose esters and acetates, aliphatic and aromatic polyamides, polyacrylonitrile, polytetrafluoroethylene (PTFE), polyvinylidene fluoride, silicone, other polymers, or other synthetic or natural materials.

Thickness of the absorbent material 104 is selected to be suitable for the analyte(s) of interest and the sampling conditions. The absorbent material 104 may range from very thin (microns) to up to approximately ¼" (though in some instances increased thicknesses may be used). As will be apparent to those skilled in the art, other thicknesses may be used as required by the specific application.

The support 102 may be a rod, cord, rope, or other suitable material for supporting the absorbent material during extraction of the sampler from the sediment. One suitable support is a Kevlar fiber. In addition or in lieu of an inner support, the sampler may comprise an external support.

Alternately, the absorbent material 104 itself may form the support such that no further support is used. For example silicone tubing or Teflon tubing may be used as the support and as the absorbent material. In such embodiment, the tubing may be solid or have a hollow center. Regardless, the tubing should be sufficiently strong to allow withdrawing from sediment without damage or breakage of the tubing. A factor in designing thickness of the tubing is that thicker tubing will enable absorption of the contaminant towards the annulus of the tubing. If the tubing is to be analyzed using fluorescence, the thickness should be such that the contaminant may not sorb so far into the tubing that it cannot fluoresce. This is not a consideration when other analysis techniques are used.

Labels or linear extent markers 108 may be provided along the length of the sampler to assist in organizing sampler segments if the sampler is cut into segments for analysis. For example, labels 108 may be provided at every foot of sampler material. The labels may be placed before or after positioning and absorption of materials. Further, the labels 108 may be placed on the absorbent material, as shown, or may be placed on the support. For example, if a substrate is used as support, the substrate may be stamped.

The sampler may be provided as a flexible continuous sampler, for example as a roll of sampler structure, that may be cut to length for particular sampling locations. The length of the sampler segments in use may vary from as short as about one meter to hundreds or even thousands of meters. The minimum length is determined by the distance over which contaminant concentration may vary. The maximum length is essentially unlimited and is determined by the desired geographical scope of the survey as well as the advantages or disadvantages of handling long segments. In a small vertical hole placement of the segments is shorter than for an extended measurement across a bottom surface, e.g. across a bay.

The sampler may include a marker 110 for indicating the sediment/water interface of the sampler 100 when positioned. The marker 110 may be, for example, a disk or other marker that is slid down the sampler once the sampler is in place. The marker 100 may incorporate a water soluble release such that the release dissolves after exposure to water, thereby locking the disk in place.

Placement of Sampler

Referring back to FIG. 1, the sampler is placed and contaminants are absorbed, shown at block 10. Sampling the contaminants may be done by positioning the sampler in the sediments and leaving the sampler for a dwell time. The sampler may be delivered by any suitable means. For example, the sampler may be hand delivered. Alternately, the sampler may be delivered using a geoprobe track rig, for example on a small shallow-draft barge. In sediments such as sands or gravels, the sampler may be impacted to aid in positioning. Generally impacted sediments are soft and readily penetrable such that the sampler may be positioned without prior drilling of an access. Alternately, an access may be drilled and the sampler delivered through the access. The sampler is positioned in a continuous manner such that each sampler extends through various depths or horizontal locations of sediment.

The sampler may be placed in locations or patterns that facilitate later mapping of the sample points. For example, the sampler may be placed in straight horizontal or vertical paths to facilitate two or three dimensional coordinate representation. It may be placed in circles or lines radiating from a defined center point. It may be placed to follow a bottom surface or a depth contour or other position represented on a map. Alternately, it may be placed in any suitable pattern to facilitate mapping.

The sampler may be positioned with a protective covering in place to prevent exposure of the sampler to contaminants during positioning. Additionally, the sampler may be positioned with a rigid support to maintain orientation of the sampler. Alternately, neither a protective covering nor a rigid support may be used.

During positioning, the depth of the water at the positioning location may be recorded. For example, a marking plate may be run down the sampler until it settles on the sediment surface. The depth of the lowered cord is then recorded. When the marking plate is retracted, a marker or clip may be secured to the sampler at the point where the marking plate was at maximum depth.

The dwell time may be for, example, as little as a few hours to as much as several days but should be sufficiently long to allow the analyte of interest to permeate the sampler. The dwell time may be, in some instances, until equilibrium is attained. Generally, the longer the dwell time, the more contaminants are accumulated. A dwell time that is excessively long may lead to saturation of the sampler in "hot spot" areas. That is, in areas of high contaminant concentration, the sampler may be saturated and unable to absorb a concentration of contaminants correlative to the contaminant concentration. A dwell time that is excessively short may result in too little absorption for analysis or a failure to absorb larger or slower contaminants. Dwell time may be determined on the basis of sampler use in similar areas. Alternately, several samplers may be placed with extraction at various times to monitor exposure and determine suitable dwell time throughout a contaminated site. Alternately, a sampler may be used having a plurality of strips, each strip having varying absorption characteristics such that after exposure, each strip may be analyzed to determine which strip's absorption characteristics are most suitable to the site. Further, trial and error may be used for determining suitable dwell time.

A combination of marker buoys and Differential Global Positioning System (DGPS) navigation may be used to mark sampler location to aid in recovery of the samplers. A rake style recovery system may alternately be used.

Analysis of Sampler

Prior to analysis, it may be desirable to rinse the sampler, shown at block 12 of FIG. 1. Rinsing the sampler removes sediments but does not effect the absorbed contaminants in the sampler. Because PDMS is hydrophobic and smooth, where a PDMS sampler is used, rinsing may be performed with little or no scrubbing.

Analysis of the sampler, shown at block 14 of FIG. 1, may be done in any suitable manner and may vary depending on the relevant contaminant.

In one embodiment, shown at block 16 of FIG. 1, analysis comprises fluorescing the sampler, for example using a UV-laser induced fluorescence. This may be done, for example, by exposing the sampler to long-wavelength mineral light (~365 nm UV lamp). Areas of the sampler with high concentrations of contaminants fluoresce more brightly than areas of the sampler with low concentrations of contaminants. Further, contaminants of different sizes may fluoresce at different wavelengths. Fluorescence is suitable, for example, for determining PAH contamination.

Contaminants existing in a non-aqueous phase liquid (NAPL) environment in the sediment, for example, in a petroleum solvent, may be differently absorbed by the sampler than contaminants existing in sediment water. Contaminants not in NAPL are transported into the sampler only by moving through the water or directly from sediment particles in direct contact with the sampler. For example, in the case of PAHs, generally, the smaller a PAH is (the less rings), the more soluble it is in water. Thus, smaller PAHs move into the sampler faster when water solubility is the controlling transport mechanism (no NAPL solvent present). Using the described methods, it is possible to differentiate light non-aqueous phase liquid (LNAPL) regions and dense non-aqueous phase liquid (DNAPL) regions amidst sediments that contain "dry" contaminants that are simply sorbed to carbon particles or other "dry" matrices, such as those carried to and deposited in sediments via soot/ash runoff, atmospheric fallout, etc. Laser induced fluorescence may be used to differentiate the products—thus, LNAPL and DNAPL source zones may be differentiated from non-point source (water soluble) affected zones.

Laser induced fluorescence (LIF) does not disturb the contaminants absorbed in the sampler. Thus, other analyses may be performed in addition to, or in lieu of, LIF. For example, in areas where NAPL is indicated via LIF, it may be desirable to perform a GC-MS analysis, shown at block 18 of FIG. 1. Similarly, areas at chosen depths or geographic locations may be chosen for GC-MS analysis to generate a calibration curve. A suitable LIF device is the Tar-specific Green Optical Screening Tool available from Dakota Technologies, Inc. of Fargo, N. Dak.

Optionally, select depths along the length of the sampler may be solvent extracted and analyzed using GC-MS. Thus, sampler segments correlative to chosen areas for GC-MS analysis may be cut from the sampler. These segments may be extracted into a solvent and introduced into a GC-MS for total quantization/speciation.

Alternately, the sampler may be read along its length with GC-MS in a continuous fashion by cryogenically trapping the desorbed contaminants as the sampler is fed through a desorbing chamber. Thus, the contaminants are integrated along a length and the cryo-trapped contaminants are thermally released into a GC-MS column for analysis.

In another embodiment, the sampler may be analyzed using an analyzer that pulls the sampler through a thermal desorption chamber. A carrier gas sweeps the volatilized contaminants, for example, volatilized PCBs, into a halogen specific detector (XSD). A suitable XSD analyzer, for example, has high selectivity to halogenated species, since a separation stage (as seen in chromatography) cannot be readily implemented in the continuous volatilization/detection mode. One suitable XSD detector is the halogen-specific detector (XSD) commercially available from Ol Analytical. The XSD has a dynamic range greater than $1 \times 10^5$ and a linear range greater than $1 \times 10^4$, 1 pg Cl/second sensitivity, and better than a $1 \times 10^4$ selectivity against non-halogenated hydrocarbons. The XSD analyzer generates an electrical current that scales with the concentration of halogenated organics in the gas stream. The current may be logged versus sampler length to produce a continuous data log of total halogenated hydrocarbon concentration versus length along the sampler—which is relatable to PCB (and/or other halogenated organics) contamination versus depth in the site. Thus, for example, heat vaporization may be used for determining PCB contamination wherein the contaminant is vaporized into a gas flow.

Again, GC-MS may be used in addition to XSD analysis for total speciation. For example, cryogenic focusing may be used and GC-MS used in addition to or in lieu of XSD for more detailed and qualitative analyses.

The analysis data may be reported in any suitable manner. Web or file-transfer-protocol (ftp) reporting may be used to make the results available in a quick manner. Colorized JPG logs may be created from the data showing a color-coded log of analyte versus depth. ASCII files may be created from the data. Such files may be integrated into geographic information system (GIS) and other data visualization systems. Bathymetry and geospatial corrections of the data may be performed using the ASCII files. The data based on GIS maps may be used for further studies, dredging, capping, in-situ remediation activities, or other.

Uses

Figure 4:
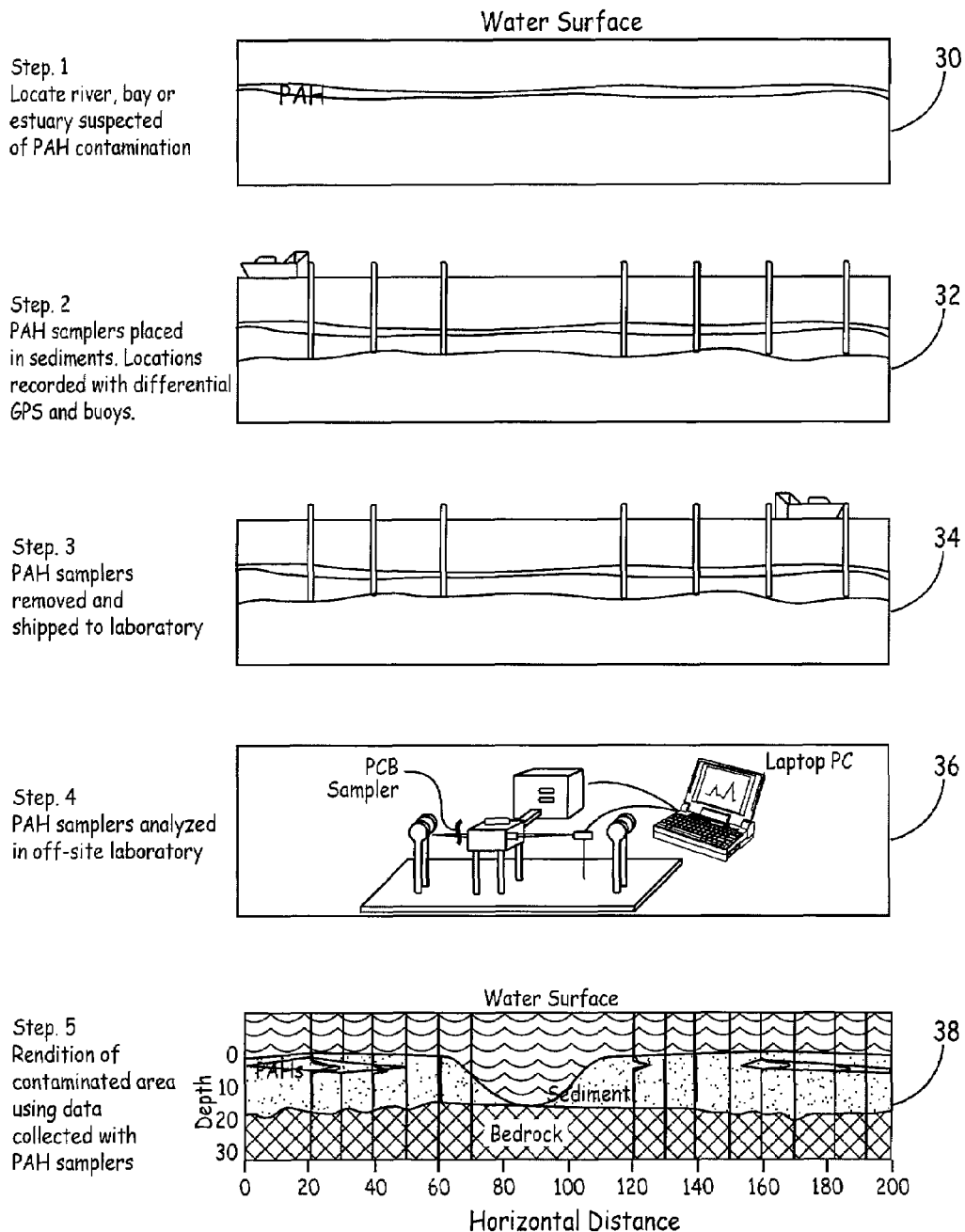
FIG. 4 is a diagram of a method of characterizing sediment contamination at a site in accordance with one embodiment of the present invention.

FIG. 4 illustrates an example of characterizing sediment contamination at a site. As shown at block 30, a site such as a river, bay, or estuary is identified as possibly being contaminated, for example, by PAHs. Other areas, including both land and bodies of water, may be analyzed using a sampler. One or more samplers are placed in a depth-continuous manner at sampling locations in sediments beneath the water surface, as shown at block 32. The sampling locations may be recorded using differential global positioning system (DGPS). Thus, the location of each sampler may be recorded using differential GPS and buoys. As discussed above, the samplers may be deployed with a sheath or protective layer. If such protective layer is used, the layer is removed to expose the absorbent sampler to the sediment. The samplers remain at the sampling locations for a dwell time. After the dwell time, the samplers are removed, shown at block 34, and analyzed, shown at block 36. Generally, analysis is performed at a laboratory. After analysis, an image of the contaminated area may be rendered using data collected with the samplers, shown at block 38.

Each sampler used may be tagged with, for example, identification numbers, DGPS location, time, date, operator, etc. The data from the sampler as well as the identification data (DGPS location, etc.) may be input into a geographic information system (GIS) visualization system.

Automated mapping and visualization of sediment contamination may be achieved using GIS software wherein visualization follows input of sampler data. Thus, using machine-vision capabilities, visualization of sediment contamination may be automated. For example, samplers bar-coded with position data supply information for use by a computer program to generate cross sections, 3 d plumes, and fence diagrams of the data.

Samplers may be positioned at numerous locations in a contaminated area to achieve an extensive mapping of sediment contamination and characterization. Thus, the methods and apparatus may be used to map and visualize contaminant distribution rather than simply to determine contaminant levels in the sediment.

Without being bound by theory, generally, except for the existence of non-aqueous phase liquids (NAPLs), the concentration gradient between the sediments and the sampler (initially at 0 ppb of analyte) drives the analytes from the sediments into the sampler. In contrast, NAPLs may physically contact the sampler and be absorbed into the sampler at rates exceeding water-soluble concentration-gradient drive processes. In accordance with a method for sediment characterization, only contaminants that are slightly soluble in water and/or are pressed directly against the membrane/sediment interface are absorbed. Thus, generally, the sampler absorbs more mobile contaminants, contaminants that are free to move about in the environment. Thus, the sampler may yield a log of contaminated zones that are of the most concern to the environment. In contrast, standard methods (such as aggressive soxhlet extractions of sediment samples) are thought to perhaps give a skewed assessment of the environmental risk posed because some of the measured contaminants are tightly bound to the sediment.

A delivery tool may be used to aid in positioning the sampler in the sediment with a minimum of streaking and smearing of the vertical horizons, thus providing a clear view of the sediment layering. For example, a delivery tube such as a stainless steel delivery tube may be used during delivery such that the delivery tube is positioned in the sediment either with the sampler provided therein prior to placement or the sampler inserted therein after placement. Regardless, once the delivery tube and sampler are in place, the delivery tube may be withdrawn with the sampler remaining in place. Further, a QA system may be used to monitor for an occurrence of streaking or smearing.

Aspects of the present teachings may be further understood in light of the following proof of concept, which should not be construed as limiting the scope of the present teachings in any way.

Proof of Concept

Figure 5:
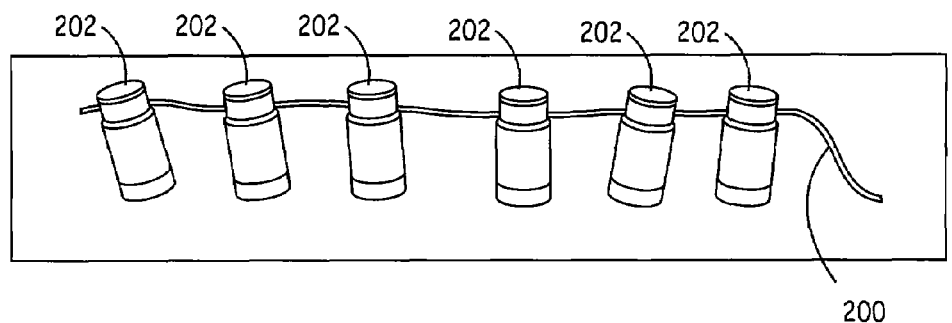
FIG. 5 is a photographic view of a sampler strung through sediment jars.

PAH contaminated sediment samples from a bay were selected for testing. The samples had already been tested for PAH content via GC-MS. The selected samples spanned a range of concentrations ranging from a relatively low 233 ppb to a high 342,000 ppb (Total PAHs by 8270C SIM). As shown in FIG. 5, each of the samples was placed in a sediment jar 202. A 3-foot section of PDMS sampler 200 was strung through each of the jars 202. A three to four inch section of PDMS sampler was imbedded into each jar. The sampler 200 was sufficiently flexible to allow full closure of caps on the jars 202. The positioning of the sampler in the jars is shown in FIG. 5.

The sampler was allowed to remain in the jars for a dwell time of approximately 16 hours. After the dwell time, the sampler was removed from the jars and sediment was rinsed from the sampler using plain tap water.

Figure 6:
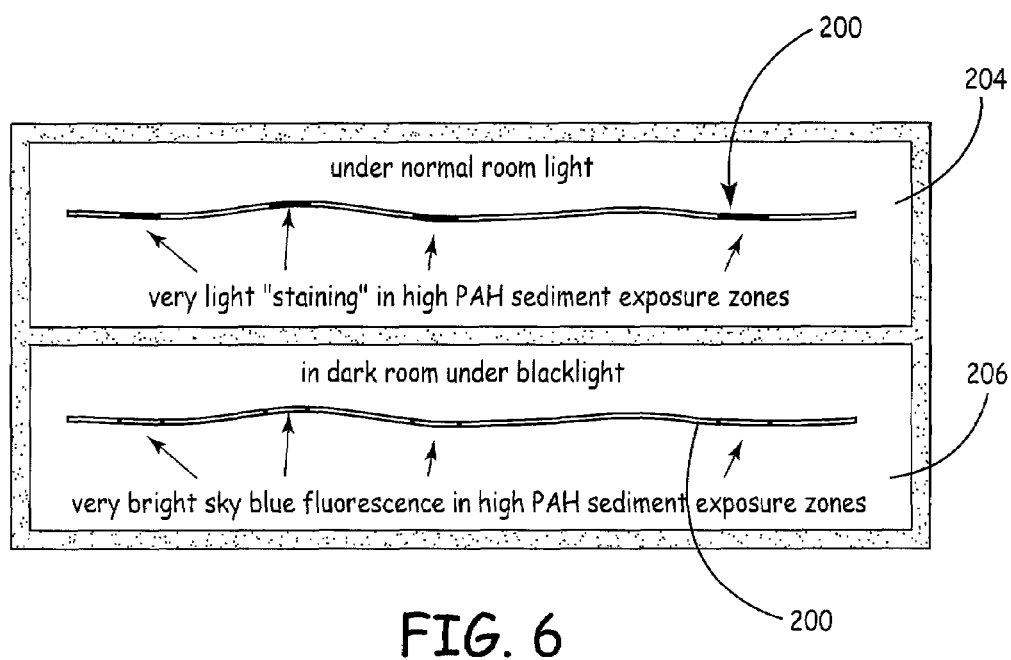
FIG. 6 is a diagram of appearance of the sampler of FIG. 5 after exposure to sediments.

A very slight amber appearance was evident in the areas of the sampler exposed to the jars with the highest PAH concentration. A computer drawing of the sampler 200 indicating the amber zones is shown in the upper panel 204 of FIG. 6.

The sampler was exposed to a long-wavelength mineral light (~365 nm UV lamp). The sections of sampler 200 exposed to a high PAH concentration glowed a brilliant blue (shown in the lower panel 206 of FIG. 6). The sections of sampler exposed to a low PAH concentration had a very low (natural PDMS background) blue haze.

Figure 7:
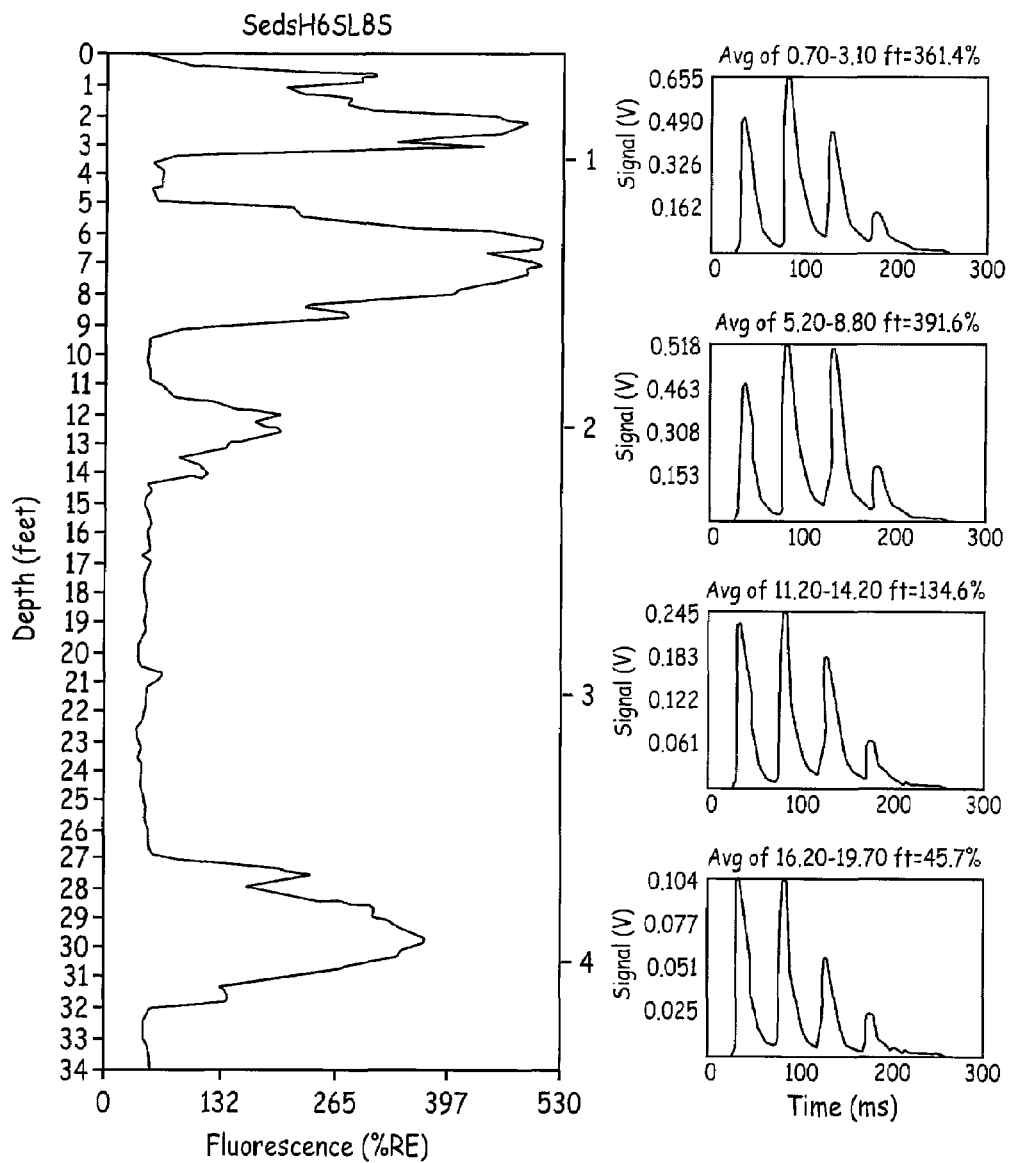
FIG. 7 is a graph showing fluorescence of the sampler of FIG. 5 with specific reference made to depths between 0.7 and 19.7 feet.
Figure 8:
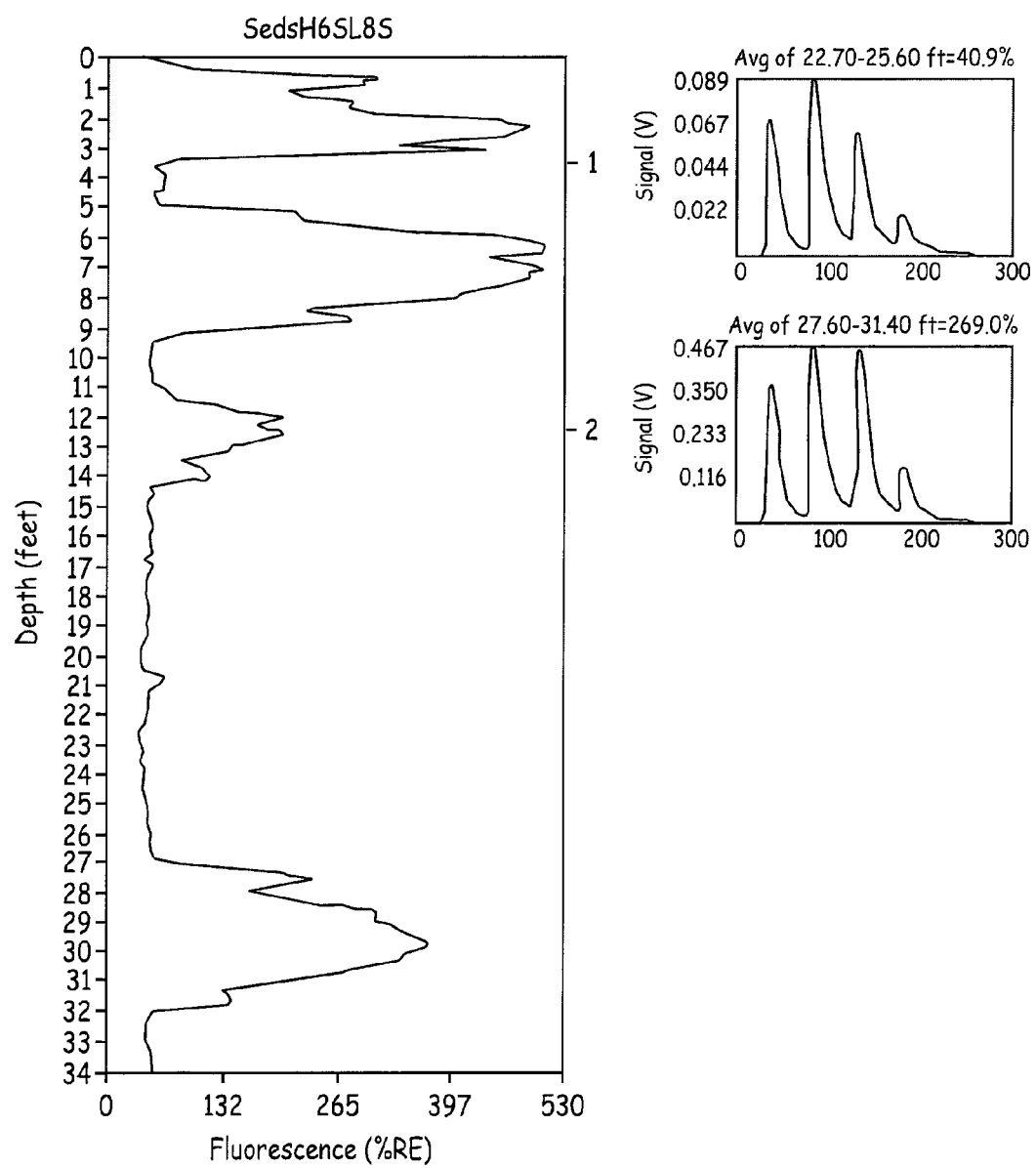
FIG. 8 is a graph showing fluorescence of the sampler of FIG. 5 with specific reference made to depths between 22.7 and 31.4 feet.

The LIF response was logged versus "depth." Note that the "depth" scale is not from a true vertical placement but instead is relative to the three-foot length of the sampler. The results of the logging are shown in FIGS. 7 and 8.

Figure 9:
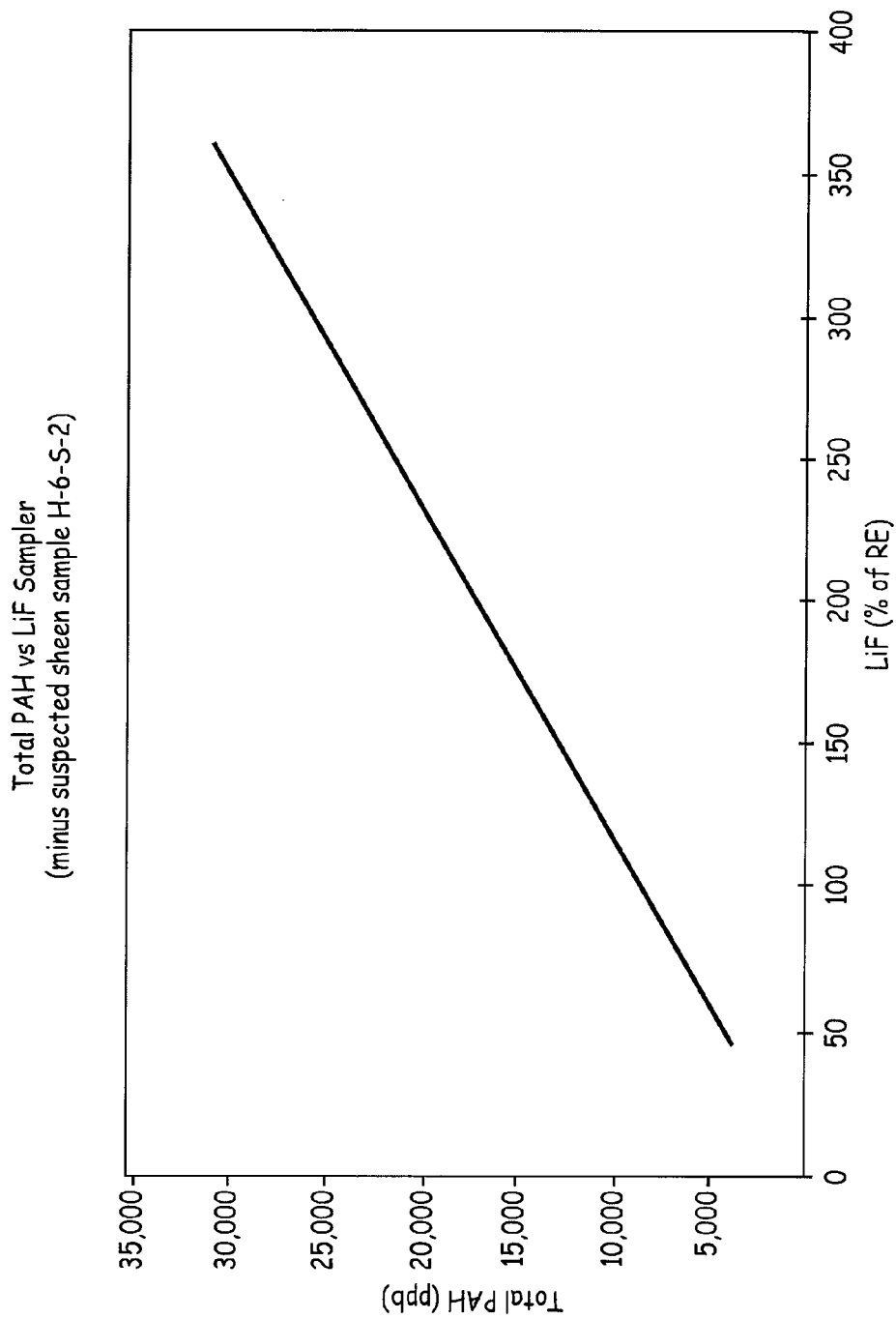
FIG. 9 is a graph plotting PAH concentration and laser induced fluorescence response for the sampler of FIG. 4.

A graph was created plotting PAH concentration and LIF response. This graph is shown in FIG. 9. The graph shows the fluorescence response taken from the LIF log of FIGS. 7 and 8 versus the total PAHs for each of the samples used.

Sample Graphs

Figure 10:
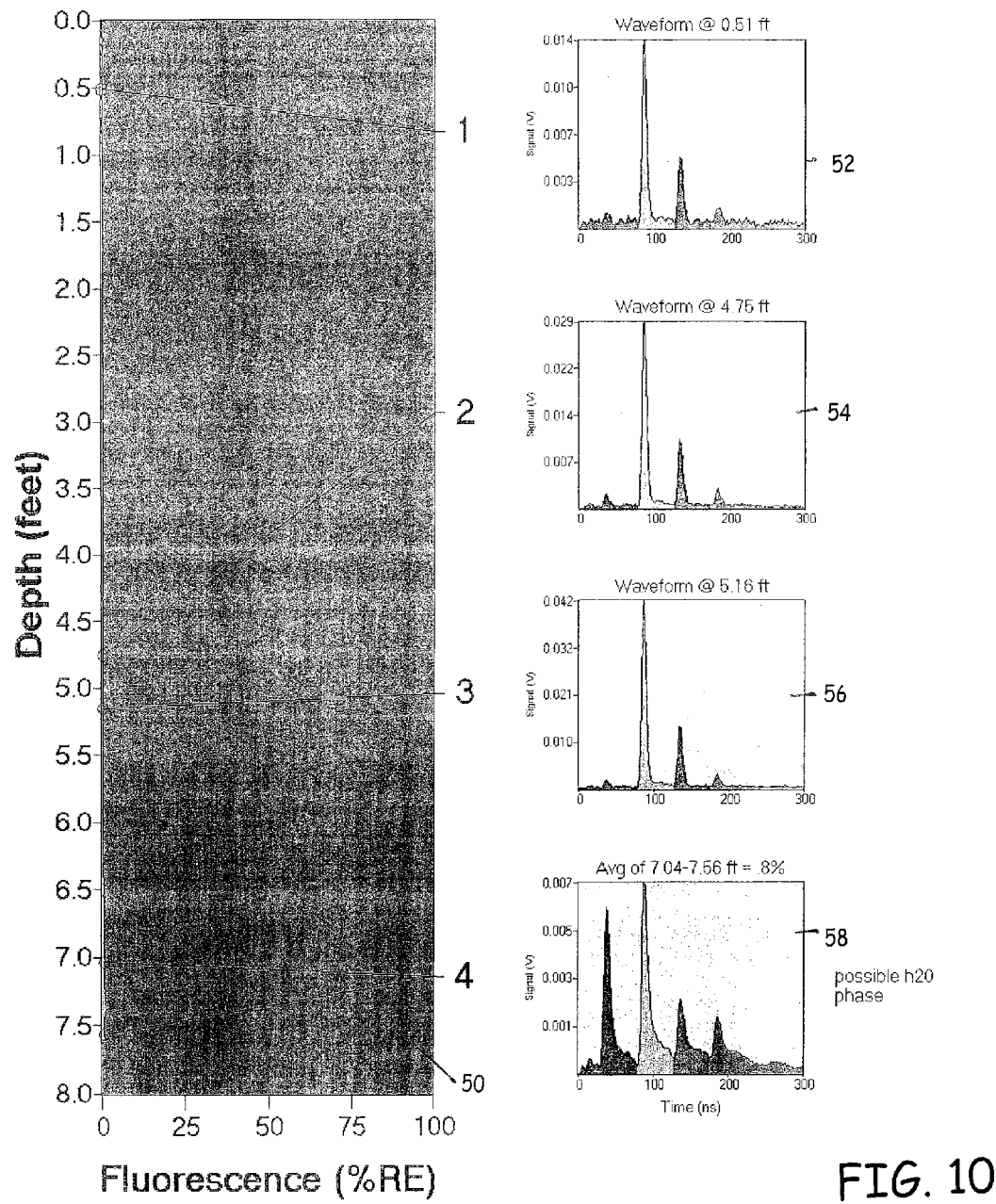
FIG. 10 is a graph showing fluorescence of a sampler placed in relatively clean sediments.

FIG. 10 shows the fluorescence scan of a sampler that was placed in sediments at a site that was a former manufactured gas plant site. The sampler was left for a dwell time of approximately 24 hours. As shown, the site was relatively clean. The graph 50 illustrates fluorescence versus depth. The graph 52 illustrates sampler readings at 0.51 feet. The graph 54 illustrates sampler readings at 4.75 feet. The graph 56 illustrates sampler readings at 5.16 feet. The graph 58 illustrates an average of the sampler readings at 7.04 and 7.56 feet.

Figure 11:
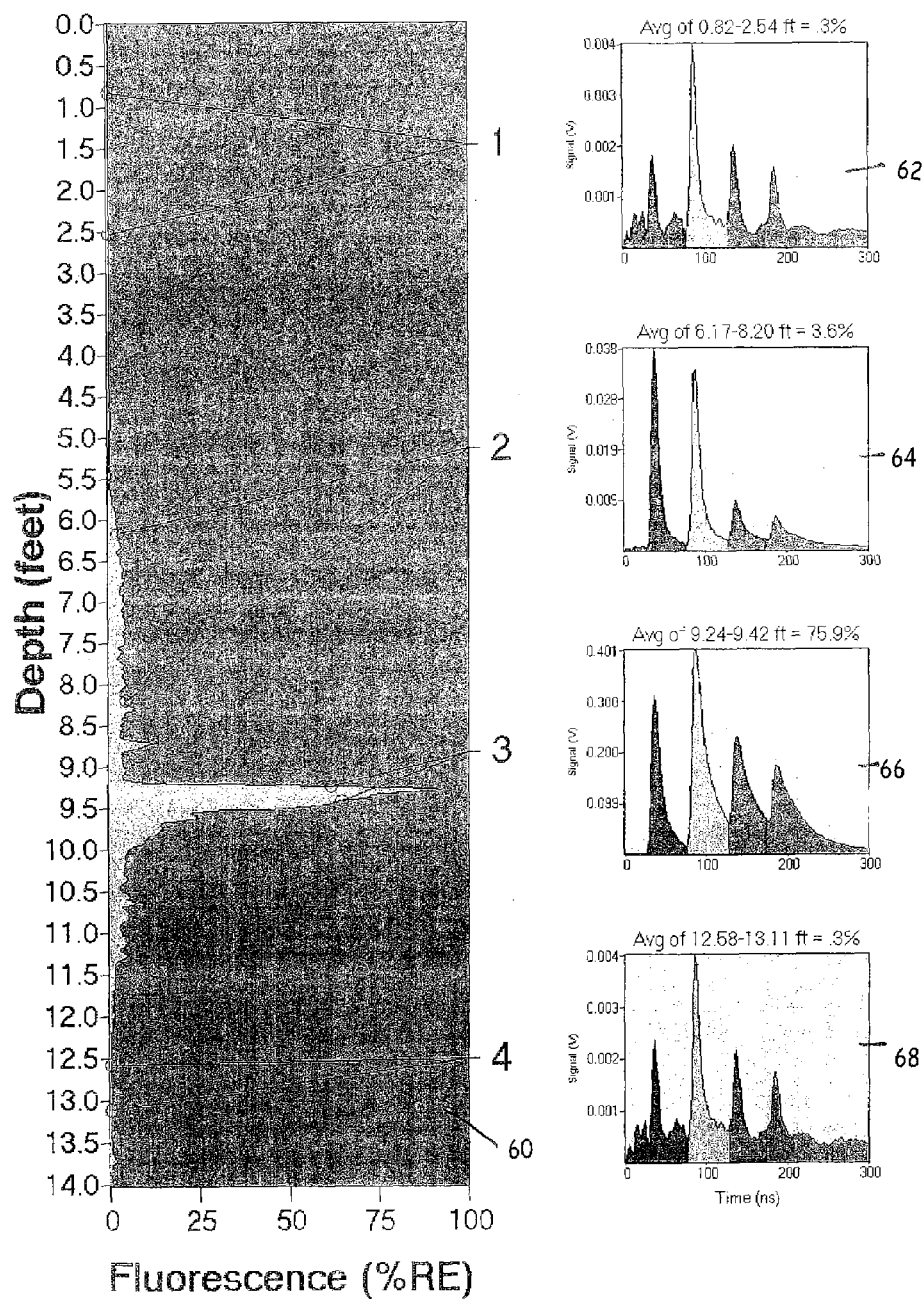
FIG. 11 is a graph showing fluorescence of a sampler placed in contaminated sediment.

FIG. 11 shows the fluorescence scan of a sampler that was placed in a site contaminated with coal tar. The graph reflects contamination of the site. The graph 60 illustrates fluorescence versus depth. The graph 62 illustrates an average of the sampler readings at 0.82 and 2.54 feet. The graph 64 illustrates an average of the sampler readings at 6.17 and 8.2 feet. The graph 66 illustrates an average of the sampler readings at 9.24 and 9.42 feet. The graph 68 illustrates an average of the sampler readings at 12.58 and 13.11 feet.

Although the present invention has been described in reference to preferred embodiments, persons skilled in the art will recognize that changes may be made in form and detail without departing from the spirit and scope of the invention.

What is claimed is:

1. A method for characterizing contaminants within sediment comprising:
    positioning an absorbent sampler in a continuous manner within the sediment, the absorbent sampler being thin and permeable only to selected analytes;
    exposing at least one continuous, extended segment of the sampler to contact with the sediment for a dwell time, thereby permitting at least one analyte to permeate and be absorbed by the sampler;
    retrieving the sampler; and
    analyzing the sampler along the extended segment by fluorescing the sampler extended segment to determine contamination versus sampler length.

2. The method of claim 1, further comprising subjecting at least a portion of the extended segment of the sampler to gas chromatography/mass spectrometry.

3. The method of claim 1, wherein analyzing the sampler comprises subjecting at least a portion of the extended segment of the sampler to gas chromatography/mass spectrometry.

4. The method of claim 1, wherein positioning the sampler comprises positioning the sampler using a rigid support.

5. The method of claim 1, further comprising rinsing the sampler after retrieving the sampler.

6. The method of claim 1, wherein exposing the sampler to the sediment comprises removing a protective sheath or layer from the sampler, the protective sheath or layer having been used to prevent exposure of the sampler to contaminants during positioning.

7. A method for characterizing contaminants within sediment comprising:
    positioning a sampler in a continuous manner within the sediment;
    exposing the sampler to contact with the sediment for a dwell time, thereby permitting at least one analyte to permeate the sampler;
    retrieving the sampler; and
    fluorescing the sampler to determine contamination versus sampler length.

8. The method of claim 7, further comprising subjecting at least a segment of the sampler to gas chromatography/mass spectrometry.

9. The method of claim 7, wherein positioning the sampler comprises positioning the sampler using a rigid support.

10. The method of claim 7, further comprising rinsing the sampler after retrieving the sampler.

11. The method of claim 7, further comprising deploying the sampler at least in part in water and providing a marker for indicating a sediment/water interface.

12. The method of claim 7, further comprising providing linear extent markers along a length of the sampler to assist in organizing sampler segments.

13. The method of claim 7, wherein the step of positioning a sampler in a continuous manner, comprises positioning an absorbent sampler made of a silicone or Teflon tubing.

* * * * *